(12) United States Patent
Fitz et al.

(10) Patent No.: US 7,968,668 B2
(45) Date of Patent: Jun. 28, 2011

(54) DIISOCYANATE TERMINATED MACROMER AND FORMULATION THEREOF FOR USE AS AN INTERNAL ADHESIVE OR SEALANT

(75) Inventors: Benjamin D. Fitz, Brooklyn, NY (US); Christopher M. Westergom, Easton, PA (US)

(73) Assignee: Ethicon Inc., Somerville, NJ (US)

( * ) Notice: Subject to any disclaimer, the term of this patent is extended or adjusted under 35 U.S.C. 154(b) by 631 days.

(21) Appl. No.: 11/476,512

(22) Filed: Jun. 28, 2006

(65) Prior Publication Data
US 2006/0280720 A1 Dec. 14, 2006

Related U.S. Application Data

(63) Continuation-in-part of application No. 11/333,057, filed on Jan. 17, 2006, now abandoned, and a continuation-in-part of application No. 11/032,332, filed on Jan. 10, 2005, now abandoned.

(51) Int. Cl.
*C08G 18/00* (2006.01)
*C09J 4/00* (2006.01)

(52) U.S. Cl. ............... 528/44; 528/52; 528/53; 528/58; 528/80; 528/81; 156/330.9; 156/331.7; 525/440.01; 525/454

(58) Field of Classification Search .................. 528/44, 528/59, 76, 52, 53, 58; 560/129, 108, 61, 560/91, 103, 106, 110, 112, 142, 145, 179, 560/180, 196, 254, 330, 359; 156/330.9, 156/331.7, 332; 525/440.01, 454, 80, 81
See application file for complete search history.

(56) References Cited

U.S. PATENT DOCUMENTS

| | | | |
|---|---|---|---|
| 3,488,376 A | 1/1970 | H. Ulrich | |
| 4,740,534 A | 4/1988 | Matsuda et al. | |
| 4,786,751 A | 11/1988 | Knofel et al. | |
| 4,804,691 A | 2/1989 | English et al. | |
| 4,806,614 A | 2/1989 | Matsuda et al. | |
| 4,829,099 A | 5/1989 | Fuller et al. | |
| 4,879,409 A | 11/1989 | Knofel et al. | |
| 4,938,763 A | 7/1990 | Dunn et al. | |
| 4,994,542 A | 2/1991 | Matsuda et al. | |
| 5,035,893 A | 7/1991 | Shioya et al. | |
| 5,118,779 A | 6/1992 | Szycher | |
| 5,173,301 A | 12/1992 | Itoh et al. | |
| 5,175,229 A | 12/1992 | Braatz et al. | |
| 5,192,536 A | 3/1993 | Huprich | |

(Continued)

FOREIGN PATENT DOCUMENTS
WO  WO 89/00589  1/1989

OTHER PUBLICATIONS

"Polymeric Biomaterials", 2$^{nd}$ Ed., Marcel Dekker Inc., (2002) pp. 716.

(Continued)

*Primary Examiner* — Milton I Cano
*Assistant Examiner* — Michael Leonard
(74) *Attorney, Agent, or Firm* — David R. Crichton

(57) ABSTRACT

A novel macromer or mixture thereof is described herein, comprising benzoyl isocyanate terminal moieties and at least two residues of a water-soluble polymer having a molecular weight ranging from 80 to 10,000 adjacent to the carbonyl group of the benzoyl isocyanate moieties, thereby forming at least two ester linkages in the macromer or mixture thereof. A method for making a polyisocyanate macromer is also described herein.

2 Claims, 5 Drawing Sheets

U.S. PATENT DOCUMENTS

| | | | |
|---|---|---|---|
| 5,457,141 | A | 10/1995 | Matsuda et al. |
| 5,486,547 | A | 1/1996 | Matsuda et al. |
| 5,584,801 | A | 12/1996 | Kuroyanagi et al. |
| 5,707,647 | A | 1/1998 | Dunn et al. |
| 5,717,030 | A | 2/1998 | Dunn et al. |
| 5,804,213 | A | 9/1998 | Rolf |
| 5,844,013 | A | 12/1998 | Kenndoff et al. |
| 5,914,125 | A | 6/1999 | Andrews et al. |
| 6,210,441 | B1 | 4/2001 | Flodin |
| 6,242,620 | B1 | 6/2001 | Elsasser et al. |
| 6,375,966 | B1 | 4/2002 | Maleeny et al. |
| 6,524,327 | B1 | 2/2003 | Spacek |
| 6,894,140 | B2 | 5/2005 | Roby |
| 7,122,205 | B2 | 10/2006 | Peterson et al. |
| 2002/0049503 | A1 | 4/2002 | Milbocker |
| 2004/0115229 | A1 | 6/2004 | Roby |
| 2004/0170597 | A1 | 9/2004 | Beckman et al. |
| 2006/0076291 | A1 | 4/2006 | Wells et al. |
| 2006/0153796 | A1 | 7/2006 | Fitz |
| 2006/0280720 | A1 | 12/2006 | Fitz et al. |
| 2006/0281874 | A1 | 12/2006 | Fitz et al. |
| 2007/0167617 | A1 | 7/2007 | Fitz et al. |

OTHER PUBLICATIONS

Organic Chemistry, J. McMurry, 2nd Edition, Brooks/Cole Publishing Company (1998) pp. 1129.

Eckert, H., et al 'Triphosgene, a Crystalline Phosgene Substitute' Angew Chem Int. Ed. Engl. (1987) vol. 26, No. 9 pp. 894-895.

International Search Report re:PCT/US2007/001247 dated Jul. 20, 2007.

International Search Report re:PCT/US2006/000674 dated May 12, 2006.

(Ic)

(Id)

IIb

DIISOCYANATE TERMINATED MACROMER AND FORMULATION THEREOF FOR USE AS AN INTERNAL ADHESIVE OR SEALANT

RELATED APPLICATION

This application is a continuation-in-part application of U.S. application Ser. No. 11/333,057, filed on Jan. 17, 2006, now abandoned and U.S. application Ser. No. 11/032,332, filed on Jan. 10, 2005, now abandoned.

FIELD OF THE INVENTION

Described herein are novel polyisocyanate macromers or mixture thereof and the use thereof to form an internal adhesive or sealant for use in cardiovascular, peripheral-vascular, cardio-thoracic, gynecological, neuro- and general abdominal surgeries. More particularly, the macromers or mixture thereof or a formulation thereof polymerizes in the human body to form an elastic gel that is biocompatible and that degrades into products that are non-toxic and biocompatible. Additionally, the degradation products are water soluble, allowing for the degradation products to be eliminated from the human body as waste products.

BACKGROUND OF THE INVENTION

Generally, the key requirements of a tissue adhesive are:
(1) In use, the adhesive must mimic the mechanical performance of the undamaged tissue;
(2) The adhesive should provide sufficient tack for "primary" fixation with the opportunity for manipulation and re-alignment prior to setting strongly;
(3) Any exothermic process involved in the curing of the adhesive should not damage the surrounding tissue;
(4) The adhesive must not elicit any toxic response by the surrounding healthy tissue and should facilitate the re-growth of new tissue where possible;
(5) The adhesive should not liberate harmful degradation products;
(6) The adhesive should degrade, and as it does so, it should be replaced by new tissue with minimal scarring; and
(7) Any biodegradation products should not accumulate in the body but should be eliminated naturally either by excretion or incorporation into the natural biochemical cycle.

["Polymeric Biomaterials", $2^{nd}$ Ed., Marcel Dekker Inc., (2002) pp. 716]

It is well known in the art that diisocyanate monomers may be used to form polymeric adhesives. However, many of the diisocyanate monomers that are commercially available are small molecule diisocyanate monomers that present toxicity and sensitization hazards and that polymerize to form products having toxic degradation products, for instance, aromatic amines. As such, commercially available small molecule diisocyanate monomers are unsuitable for human use as an internal adhesive or sealant.

Metabolically acceptable polyisocyanate monomers are described in U.S. Pat. No. 4,829,099. More specifically, this reference describes an aromatic benzoyl isocyanate terminated monomer, having glycolic acid residues and polyethyleneglycol residues, in formula "I, Preferred". This reference indicates that the resultant polymer will degrade ultimately to metabolically acceptable products, including p-aminobenzoic acid, polyethylene glycol and glycolic acid. Although the resultant polymer in principal could degrade into the aforementioned compounds, it is believed that only the glycolic acid residues would hydrolyse in vivo, resulting in a mixture of water-soluble and water insoluble fragments. The water-soluble fragments would be eliminated naturally by excretion from the body. However, the water insoluble fragments would not be eliminated naturally, resulting in the undesirable accumulation of the water insoluble fragments in the body.

Polyester-urethane-urea block copolymers prepared from commercially available small molecular diisocyanates, i.e. tolylene diisocyanate (TDI), diphenylmethane-4,4'-diisocyanate (MDI), and hexamethylene disisocyanate (HMDI), are described in U.S. Pat. No. 6,210,441. However, these copolymers would be unsuitable for use as a surgical adhesive or sealant, since the copolymers are already polymerized, i.e., already cured, and would not provide sufficient opportunity for manipulation and re-alignment. Moreover, such copolymers are not believed to mimic the mechanical performance of undamaged tissue.

Therefore, it is desirable to have a monomer based internal adhesive or sealant formulation that is capable of polymerizing in vivo to form an internal adhesive or sealant, in order to provide an opportunity for manipulation and re-alignment. Specifically, it is desirable that the adhesive or sealant formulation fill internal cavities and voids, penetrating and conforming to the interstices and pores of the tissue, prior to curing or setting.

Additionally, it is desirable to have a monomer based internal adhesive or sealant formulation that polymerizes in vivo, where the monomer, the formulation thereof, and the resultant polymer are biocompatible. The resultant polymer should also be biodegradable.

Finally, it is desirable that the degradation products of the resultant polymer be both biocompatible and water soluble, so that the degradation products are completely eliminated from the human body as waste products.

SUMMARY OF THE INVENTION

Novel macromers or a mixture thereof are described herein, comprising benzoyl isocyanate terminal moieties and at least two residues of a water-soluble polymer having a molecular weight ranging from 80 to 10,000 adjacent to the carbonyl group of the benzoyl isocyanate moieties, thereby forming at least two ester linkages in the macromer.

Definitions

Unless defined otherwise, all technical and scientific terms used herein have the same meaning as is commonly understood by one of skill in the art to which this invention belongs. All patents and publications mentioned herein are incorporated by reference.

"Biocompatible" as used herein refers to a material that, once implanted, does not interfere significantly with wound healing and/or tissue regeneration, and does not cause any significant metabolic disturbance.

"Biodegradable" and "bioabsorbable" as used herein refer to a material that is broken down spontaneously and/or by the mammalian body into components which are consumed or eliminated in such a manner as not to interfere significantly with wound healing and/or tissue regeneration, and without causing any significant metabolic disturbance.

"Water-soluble polymer" as used herein refers to a polymer, which dissolves in water, forming transparent solutions under ambient conditions (e.g. body temperature).

"Polyisocyanate" as used herein refers to a compound with two or more isocyanate groups.

"Urethane linkage" as used herein refers to a residue derived from a urethane moiety and having a carbonyl-containing functional group in which the carbonyl carbon is bound both to an ether oxygen and to an amine nitrogen:

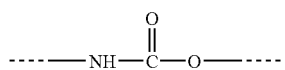

["Organic Chemistry", J. McMurry, 2$^{nd}$ ed., Brooks/Cole Publishing Company, (1988), pp 1129].

"Urea linkage" as used herein refers to a residue derived from a moiety having a carbonyl-containing functional group in which the carbonyl carbon is bound to identical units of amine nitrogen:

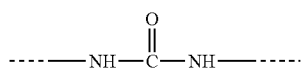

["Nomenclature of Organic Chemistry", Pergamon Press, Oxford, (1979)].

DETAILED DESCRIPTION OF THE INVENTION

Figure 1:
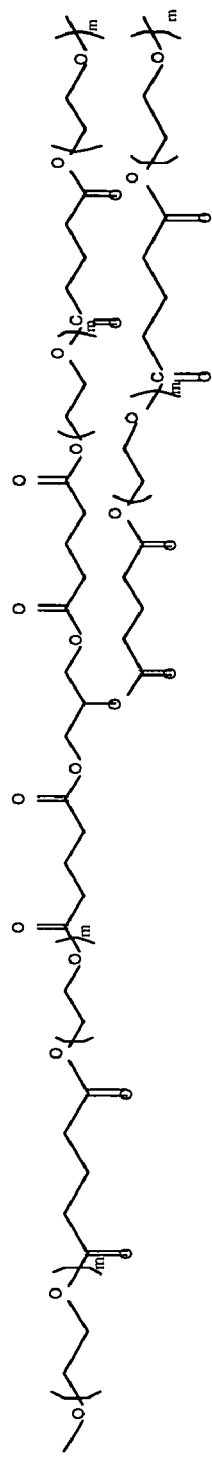
FIG. 1 is an example of a branched $R_2$ residue.

As described above, a monomer based internal adhesive or sealant formulation that is capable of polymerizing in vivo to form an internal adhesive or sealant, should wet the tissue to which it is applied, penetrating and conforming to the interstices and pores of the tissue, prior to curing or setting. Additionally, the monomer, the formulation thereof, and the resultant polymer should be biocompatible.

The monomer and the formulation thereof described herein are suitable for internal applications, since neither the monomer, the formulation thereof nor the resultant polymer metabolizes in the human body to form toxic products.

Additionally, the monomer and the formulation thereof polymerize to form a biocompatible polymer upon contact with water or body fluids. The biocompatible polymer then degrades in vivo to form degradation products that are both biocompatible and water soluble, which are then eliminated from the human body as waste products.

The monomer and the formulation thereof have multiple medical applications and may be used in many types of surgery, including, but not limited to, cardiovascular, peripheral-vascular, cardio-thoracic, gynecological, neuro- and general abdominal surgery.

For example, the monomer and the formulation thereof may be used as an internal surgical adhesive in orthopedic procedures such as anterior cruciate ligament repair, meniscal tear repair (or as a hydrogel for the replacement of the meniscus), posterior capsule reconstruction, rotator cuff repair, and as a bone adhesive. It could also be used as an adhesive for lung volume reduction, patch fixation, subcutaneous tissue repair, and aortic dissection. In particular, it can be used as stomach adhesive for stomach volume reduction, and as adhesive for mesh fixation for hernia repair, drain fixation, valve attachment, attachmerit for adhesion prevention films, attachment of tissue to tissue (e.g. synthetic or biologic tissue scaffold to tissue, bioengineered tissue to tissue), tissue to device (e.g. mesh, clip, film) and device to device.

Second, the monomer and the formulation thereof may be used for subcutaneous tissue repair and for seroma prevention in procedures such as mastectomy, breast reconstruction & augmentation, reconstructive or cosmetic abdominoplasty and liposuction, face lift, C-section, hysterectomy in obese patients, orthopedic on thigh region, incisional hernia repair, lipoma excision, traumatic lesions, fistula treatment, graft fixation, and nerve repair.

Third, the monomer and the formulation thereof may be used as a sealant to attach and seal dural patch products, bile duct, bile leaks in liver bed, bladder leaks, bone graft, burn graft dressing and liquid occlusive dressing. As a sealant, it can be coated on tissue, device, and tissue-device interface and it can be used as dural—cranial sealant, dural—spine sealant, cardio/peripheral vascular sealant, GI sealant (e.g. esophagus, intestine, large organ, pancreas, stomach, and gastric ulcer), lung sealant, soft organ sealant (e.g. liver, spleen, pancreas), bonewax substitute, tumor sealant, staple/glue combination, sealant/hemostats combination, urethra sealant. It can be used in procedures including, but not limited to, gastric bypass, parenchymatous organs resection, tracheostomy, ulcerative colitis diverticulosis, radical prostatectomy, sinus reconstruction, sternotomy, choledochoduodenostomy, and gallbladder (liver) bed sealing, and cholecystectomy.

Fourth, the monomer and the formulation thereof may be used as a filler or a periurethral bulking agent in procedures including, but not limited, to dead space removal in reconstructive and cosmetic surgeries, (e.g. plastic/cosmetic/reconstructive, face/facial defect, or void filling), urinary incontinence and other gynecologic procedures, anal fissure/fistula, catheter injection into myocardium for treating congestive heart failure, nuclear augmentation, pancreatic/hepatic cyst/fistula obliteration, and pediatric esophogeal fistula.

Fifth, the monomer and the formulation thereof may be used as a matrix for tissue engineering (e.g. tissue scaffolds, delivery matrix for cells, delivery matrix for brachytherapy (radiation therapy) agents, delivery matrix for growth factors, injection matrix for in situ-forming empty cell scaffold, injection matrix for scaffold for delivery of stem cells, cell lysate, or other biologics, bioactives, pharmaceuticals, and neutraceuticals, localization matrix for chemotherapy, and localization matrix for contrast agent.

Sixth, the monomer and the formulation thereof may be used as an adhesion prevention barrier in procedures such as cardiac, open chest, general surgery, obstetrics and gynecological surgeries, orthopedic surgeries, and spine (e.g. artificial disk).

Seventh, the monomer and the formulation thereof may be used as an occluding material for embolization (e.g. GI Fistula, cerebral/vascular occlusive brain aneurism, tubal occlusion, and varicose vein occlusion).

Macromer

The monomer described herein is a biocompatible polyisocyanate macromer, terminating with benzoyl isocyanate groups and having the structural formula I:

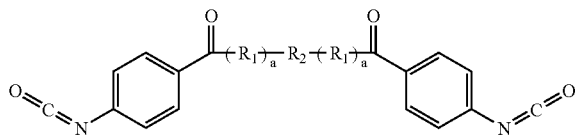

(I)

where $R_1$ is an organic residue containing a urethane linkage that is attached to $R_2$ when the value of "a" is one or more, and preferably one to five. The value of "a" in formula I may also be zero.

The macromer may also be a polyisocyanate macromer represented by formula II:

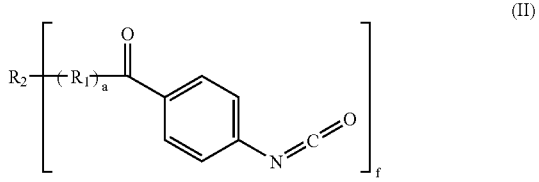

(II)

Wherein f represent the number of end-groups in the macromer.

When f=2, formula II represents a linear macromer, when f is three or more, formula II represents a branched macromer.

An example of $R_1$ when "a" is one or more is shown below:

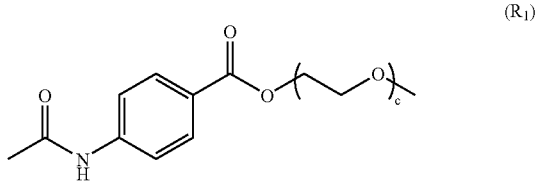

($R_1$)

where the ethylene oxide portion of $R_1$ may be linear or branched, and c may range from 1 to 100, and preferably from 1 to 10.

The general structure of $R_2$ in formula I is the following:

$$-R_3-R_4-R_3-\quad (R_2)$$

Where $R_2$ in formula I has hydrolysable ester linkages that are biodegradable in vivo; $R_3$ may be residue of a water soluble polymer, including but not limited to a residue of a polyalkylene glycol such as polyethylene glycol, a polyalkylene oxide, polyvinylpyrolidone, poly(vinyl alcohol), poly (vinyl methyl ether), polyhydroxymethyl methacrylate, a polyacrylic acid polymer and copolymer, polyoxazoline, polyphosphazine, polyacrylamide, a polypeptide, or the water-soluble derivatives of any of the above, that is capable of forming ester linkages together with $R_4$, and (i) ester linkages together with the carbonyl group of the benzoyl isocyanate moiety when "a" is zero or (ii) urethane linkages together with R1 when "a" is one or more. Further, $R_3$ may be linear or branched. When $R_3$ is a polyethylene glycol residue,

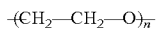

and "a" is one or more, n should be sufficiently large to render the degradation product IV (shown below) water soluble. For example, n may range from 2 to 250, preferably from 5 to 100, and more preferably is 5 to 25. The molecular weight of R3 may range from 80 to 10,000, preferably 200 to 4000, and more preferably 200 to 1000. These residues of water-soluble polymer must be coupled into the macromer in the R3 position and are critical to the solubility of the degradation products, as will be discussed in more detail below.

R4 may be an organic residue capable of having carboxylate end-groups. For example, R4 may be derived from linear diacids, such as diglycolic acid, malonic acid, glutaric acid, succinic acid, adipic acid, or carboxylic acid terminated-polyalkyleneglycols such as polyalkylene glycol dicarboxylates.

If R4 is an aliphatic dicarboxylate:

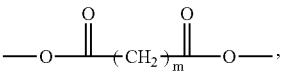

m may range from 1 to 10. The selection of m is based on two factors: biocompatibility and solubility of degradation products. If m is 0, the diacid hydrolytic degradation product of the macromer is too acidic, thus detrimental to biocompatibility of the composition. If m is too large, the diacid degradation product will no longer be water soluble.

Alternatively, R4 may be derived from a branched acid such as tricarballylic acid, citric acid, or tartaric acid or the glutaric anhydride derivative thereof. Alternately, R4 may be derived from any of the aforementioned acids, carboxylic acid terminated-polyalkyleneglycols or glutaric andhydride derivative, resulting in a compound with carboxylate end-groups. Additional examples of R4 are shown below:

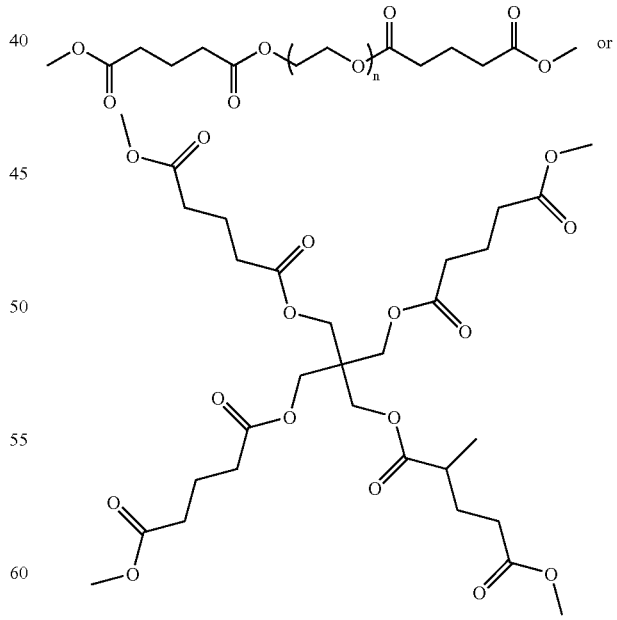

Alternately, R2 may be formed from any carbonyl-containing moiety via synthetic routes (including but not limited to trans-esterification, acid halide-alcohol condensation, acid-alcohol condensation) resulting in ester linkages to R3.

Examples of R2 includes but is not limited to a residue of a PEG-ester made from the polycondensation reaction of polyethylene glycol and a compound bearing multiple carboxylic groups, wherein the carboxylic group containing compounds include but are not limited to diglycolic acid, malonic acid, succinic acid, glutaric acid, adipic acid, tartaric acid, and carboxylic acid terminated-polyalkyleneglycols.

Examples of a PEG-ester version of $R_2$ residue include but are not limited to:

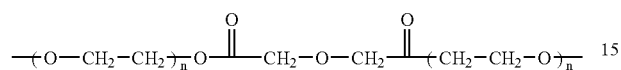

(a)

where n is 20 for PEG of Mw 900 and the diacid is diglycolic acid

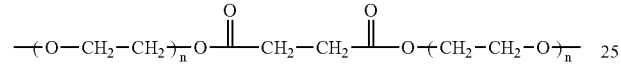

(b)

where n is 20 for PEG of Mw 900 and the diacid is succinic acid

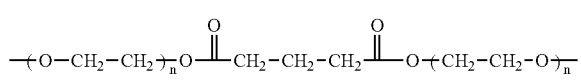

(c)

where n is 20 for PEG of Mw 900 and the diacid is glutaric acid

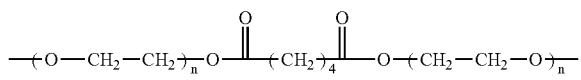

(d)

where n is 20 for PEG of Mw 900 and the diacid is adipic acid

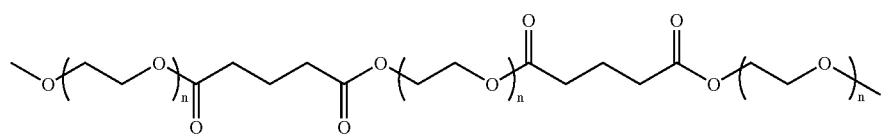

(e)

Other examples include branched $R_2$ residues are shown below and in FIG. 1:

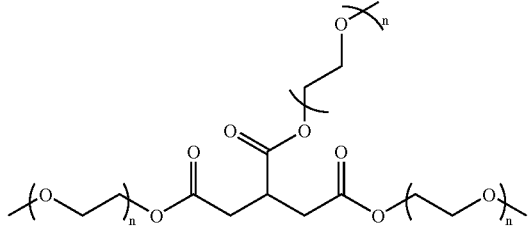

(f)

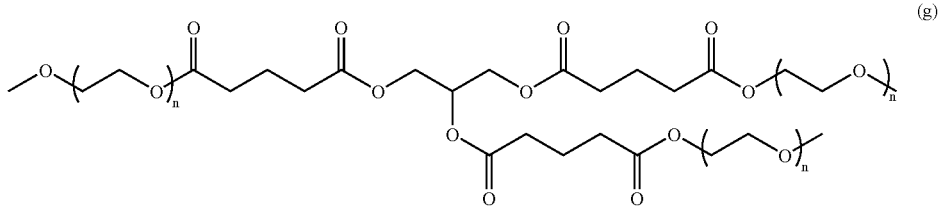

(g)

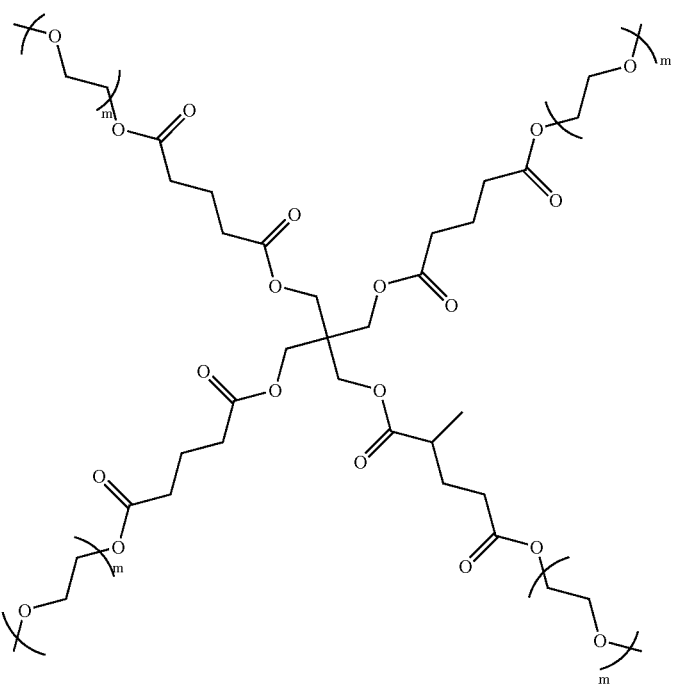
(h)
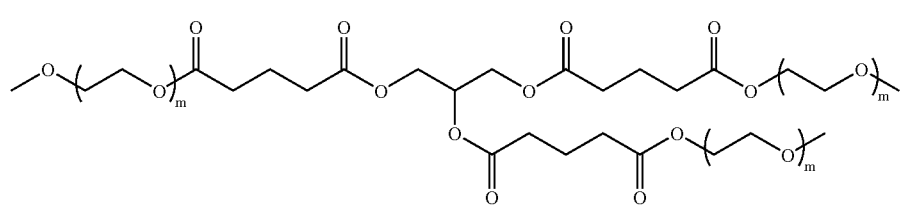
(i)
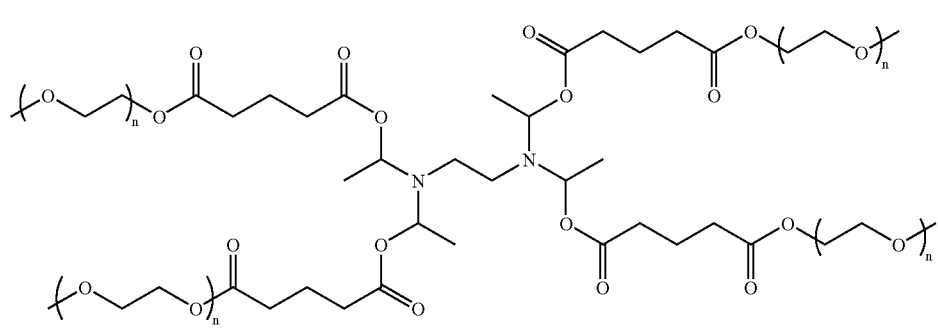
(j)
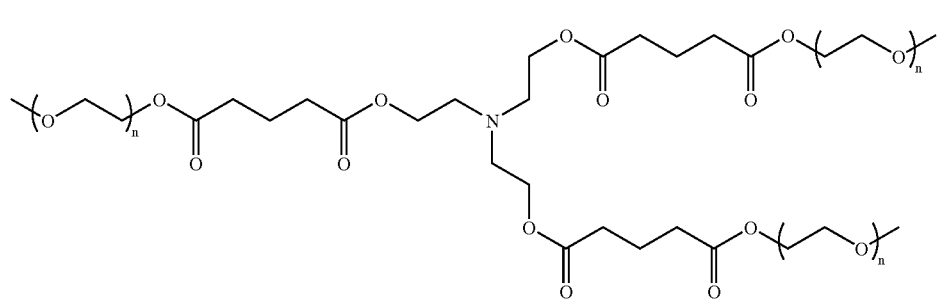
(k)
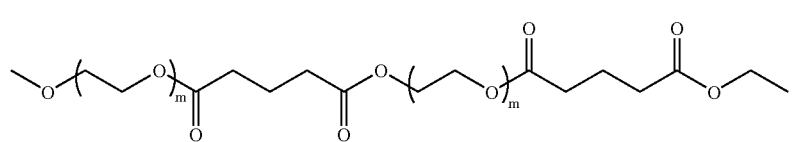
(l)

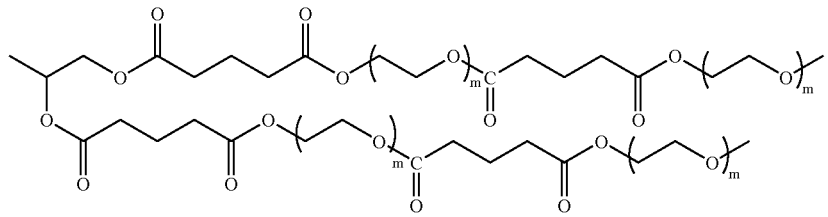

(I)

The molecular weight of the $R_2$ residue portion of the macromer may range from about 80 to 20,000 g/mol.

Producing a polyester polyol from which $R_2$ may be derived in high yield requires the use of a transition metal catalyst such as tin (II). Tin salts are well known as catalysts for esterification. They are hydrolytically stable and can withstand moisture generated during esterification without any loss of activity. They are more desirable to use than acid catalysts such as p-toluenesulfonic acid or mineral acids because these materials promote ether cleavage as well as oxidiation, especially at higher temperatures. Typical temperatures during esterification of the polyols and polyacids range from 160-220° C. It is desirable to obtain a polyester polyol that contains as little oxidation side products as possible as this will affect the performance of the macromer. Tin catalysts also significantly reduce reaction times. Typical times to reach the desired polymer molecular weight and acid content range from 12-18 hours. To achieve a similar product without catalyst would require more than 60 hours. However, tin metal is toxic and must be removed from the polyol once esterification is complete.

Removing the tin catalyst after the reaction is completed poses a unique problem because regular methods to remove the catalyst are not as effective in polyester polyols. A common method is to use a small amount of hydrogen peroxide to oxidize the tin to an insoluble tin oxide, which can be filtered off. This is undesirable as treating any polyethylene glycol containing material with a peroxide will accelerate the formation of carbonyl and peroxide groups, which are undesirable impurities. Washing the material with water does not work either because the material itself is hydrophilic and tin is not easily hydrated. Adding a mineral acid to neutralize the tin is undesirable, as it will also hydrolyze eater bonds in the polymer. It is therefore desirable to find a mild adsorption agent that will selectively remove tin.

Citric acid can be used to chelate the tin catalyst, followed by treatment with silica to adsorb the tin citrate complex. Preferably a mixture of citric acid and silica is used. More preferably, a silica hydrogel treated with citric acid sold under the trademark Sorbsil R® by Ineos Silicas is used in the edible oils industry to remove trace metals and other polar impurities. The material is described as a silica hydrogel that is treated with citric acid. Citric acid is a known chelating agent and when covalently bound to silica, it increases the effectiveness of chelating metals such as tin compounds that are not as easily hydrated. Additionally, the polyester polyols have a high affinity for the tin catalyst since concentrations as high as 700 ppm of tin in the polymer are clear and free of sediment, which is not typical. Quantities from 0.01-1.00% by weight of oil can be used to effectively remove undesired impurities in the oil. This silica/citric acid mixture is suitable for removal of tin II & IV, both of which are common catalysts used in esterification. By treating a crude tin catalyzed polyester polyol with silica/citric acid, the tin can be adsorbed and filtered off leaving the metal free polyol. An organic solvent, such as toluene is necessary to aid in filtration because the silica/citric acid/tin complex is partially soluble in the polyester polyol. Since the silica/citric acid mixture is hydrophilic, it is necessary to add a hydrophobic solvent that will solublize the polyester polyol and precipitate the silica-citric acid hydrogel. The hydrophobic solvents include, but not limited to, benzene, toluene, xylene, methylene chloride and chloroform. Addition of the solvent precipitates the complex facilitating filtration. Other materials, such as carbon powder and diatomaceous earth can be added during treatment to improve color and filtration times. Use of this method of tin removal results in a polyester polyol free of tin with no significant increase in acid content, which is a sign of hydrolysis. Typical polymers worked up in this manner have contained less than 5 ppm of tin (600 ppm tin before treatment), ~99.5% conversion of acid groups to ester groups (~99.8% conversion before treatment) and no significant evidence of carbonyl groups when analyzed by proton NMR.

For instance, a crude polyester polyol is treated with 1-10% by weight of a silicate, 0.05-1.00% by weight of carbon and 0-1% by weight of diatomaceous earth. The slurry is stirred for 30-90 minutes under an inert atmosphere at 60-85° C. The polymer is diluted to 40-60% by weight using a suitable organic solvent then filtered. The solvent is evaporated to yield the desired polyester polyol with low tin.

Examples of linear macromers include those shown in Formulae Ia and Ib.

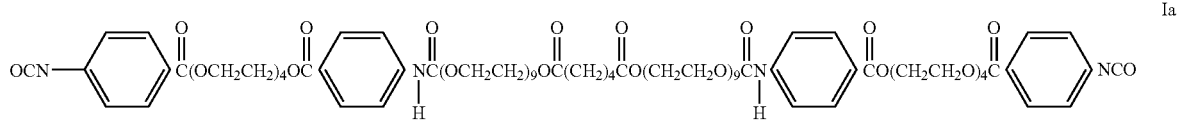

Ia

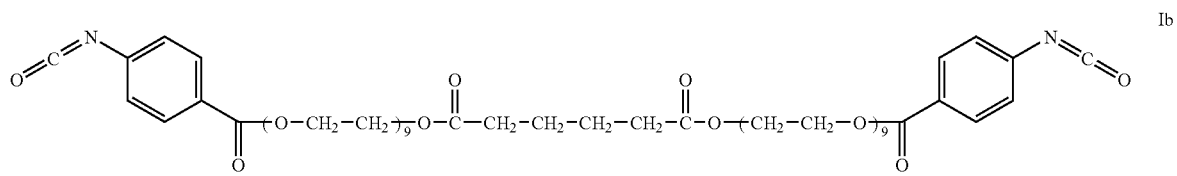

Figure 2:
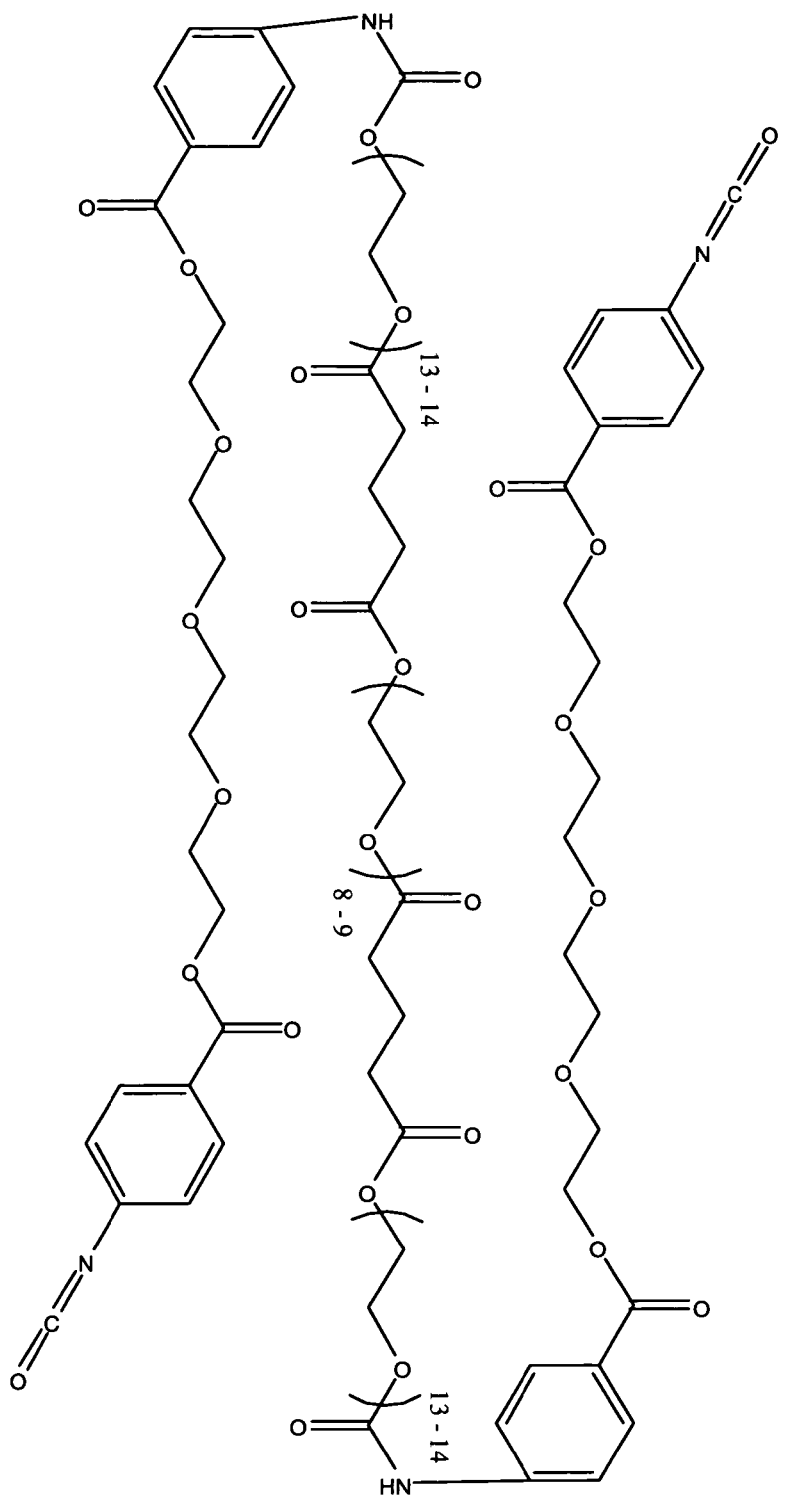
FIG. 2 is an example of a preferred macromer Ic for a surgical sealant application giving high intestinal burst strength.
Figure 3:
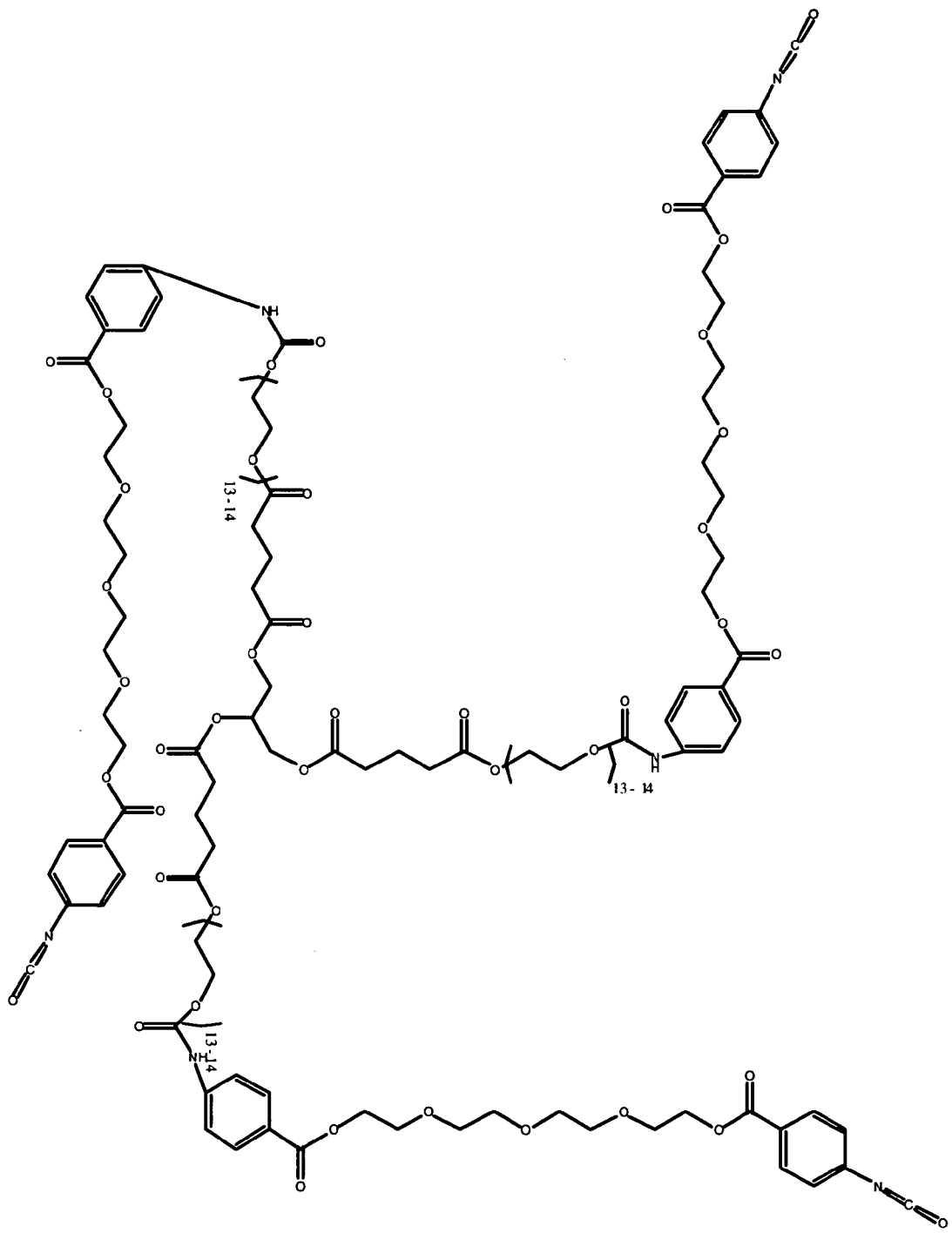
FIG. 3 represents macromer Id.

An example of a preferred macromer for a surgical sealant application giving high intestinal burst strength is shown in FIG. 2 as Ic. A preferred macromer composition is a mixture of macromers Ic and Id (as shown in FIG. 3) in a 1:1 molar ratio.

An example of a branched macromer is IIa:

Wherein the intermediate polyol has $g+1$ hydroxyl end groups.

The molecular weight and degree of branching of the macromer are an important factors for determining biomechanical properties, such as elasticity, adhesive and cohesive strength, viscosity, absorption and water-uptake (swelling).

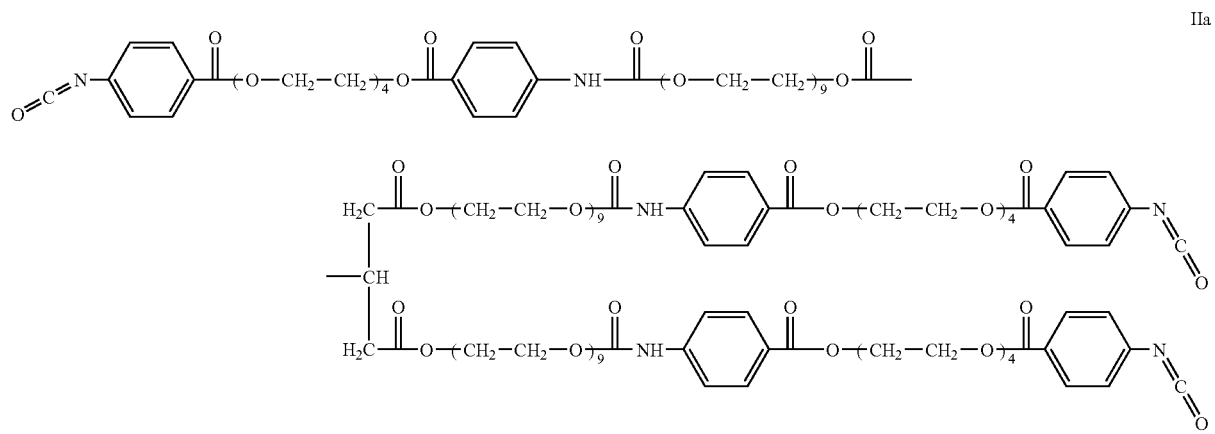

Figure 4:
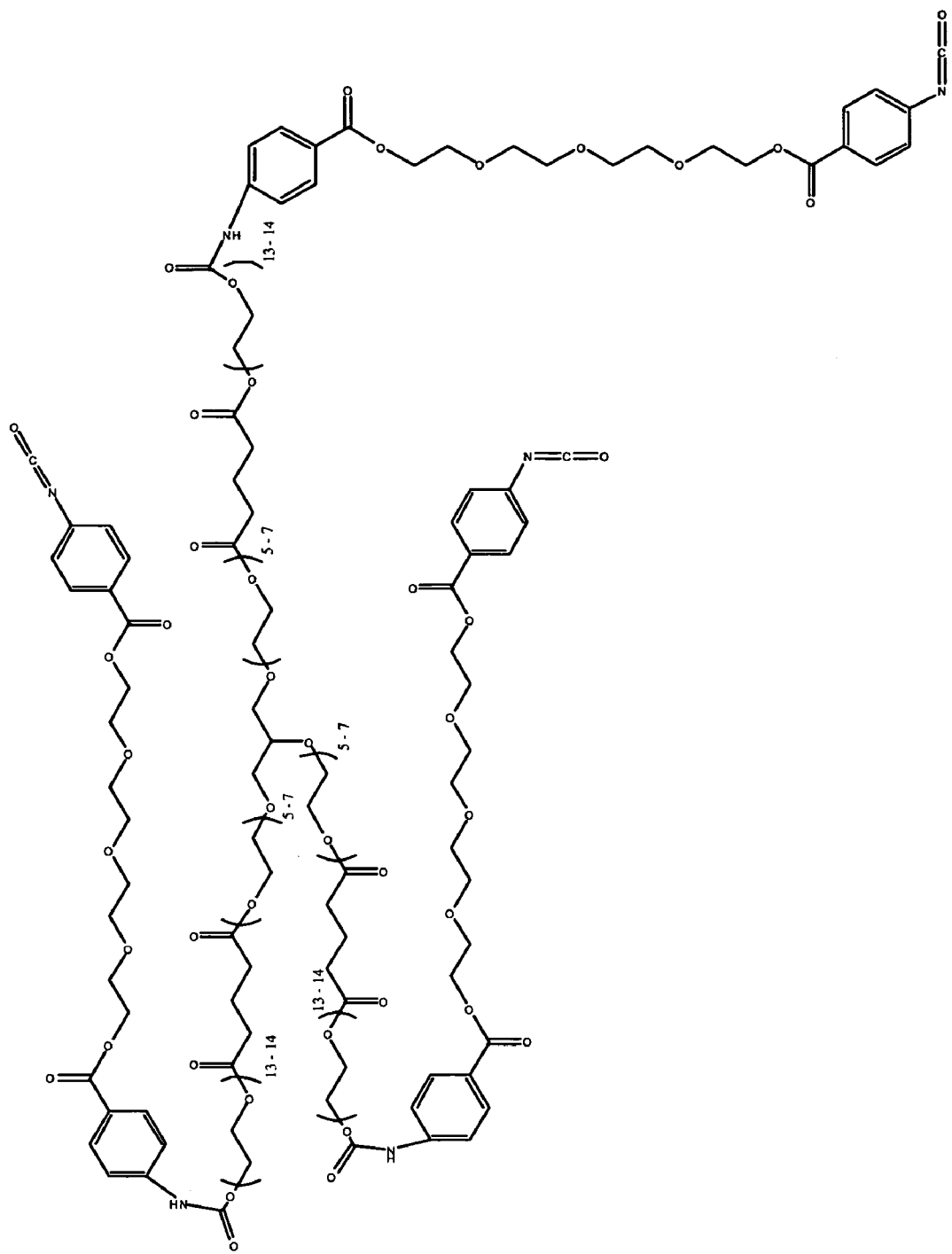
FIG. 4 is a preferred branched macromer IIb for intestinal burst strength.

A preferred branched macromer for intestinal burst strength is shown in FIG. 4 as IIb.

An alternative type of branched macromer is shown below as III. These are prepared by coupling an excess of linear isocyanate-terminated macromers of formula I with a multifunctional active hydrogen-terminated compound, such as a hydroxy-terminated compound, as shown here in $R_6$:

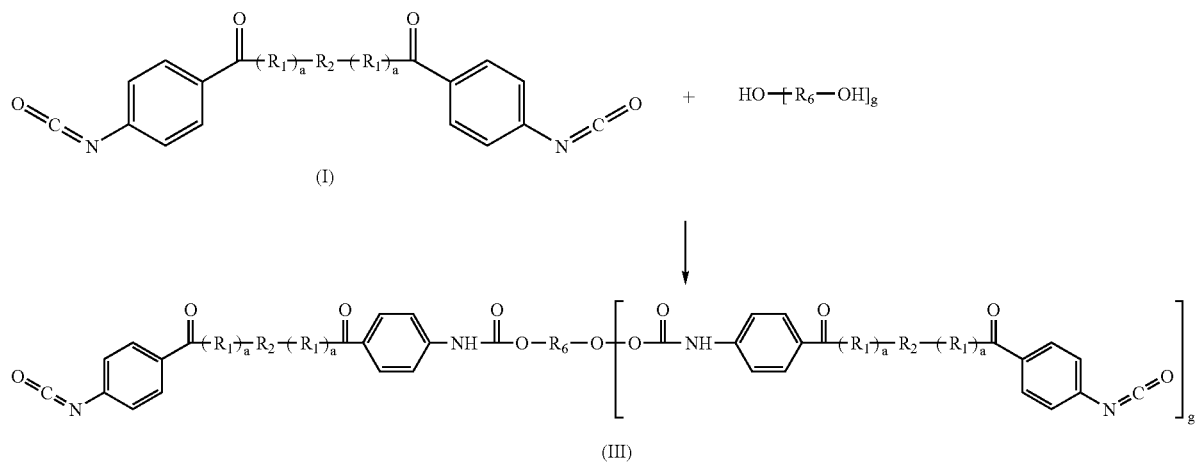

TABLE 1

Desirable Property Ranges for Intended Use of the Composition

| Property | Range | Preferred Range for Sealant | Preferred Range for Adhesive |
|---|---|---|---|
| elasticity[1] | 10-2000% | 50-500% | 10-50% |
| adhesive strength[2] | burst pressure: >200 mmHg | >200 mmHg | lap shear tensile strength >1 Mpa |
| cohesive strength[3] | 0.1-30 Mpa | 0.1-5 Mpa | 5-25 Mpa |

[2]Adhesive strength quantifies the ability of the adhesive/sealant material to adhere to the biological tissue. It is measured by the fluid burst pressure test-ASTM 2392-04 - Burst pressure testing is performed by cutting a linear incision of 0.5 cm in a substrate (pericardium, dura or collagen) and placing the substrate in a test fixture. Sealant is applied to the incision and allowed to cure. Increasing pressure is applied to the transverse side of the substrate using a syringe pump filled with fluid. The maximum pressure is recorded when the sealant ruptures.
[1,3]Cohesive strength refers to the intrinsic ability of adhesive/sealant material to withstand tensile forces. Cohesive strength and elasticity are measured by Elongation and Modulus - Tensile specimens of cured sealant are prepared by casting as a film. The samples are tested in tension at 1 inch/minute until failure. The maximum load and elongation at failure are recorded.

The range of the molecular weight of the macromers described herein may be between about 500 to 20,000 g/mol, and preferably between about 500 and about 4000 g/mol.

Macromer-Containing Formulation:

A medically acceptable formulation may comprise the polyisocyanate macromer, a solvent, a catalyst, a surfactant, a stabilizer or antioxidant, and a color additive.

Typically, the solvent is a hydrophilic solvent, including but not limited to dimethyl sulfoxide (DMSO), acetone, dimethoxy PEGs, glycerine, Tween 80, dimethylisosorbide, propylene carbonate, and 1-methyl-2-pyrrolidinone (NMP). Less hydrophilic solvents may also be considered, such as: ethyl lactate, triacetin, benzyl alcohol, benzylbenzoate, various ester solvents, such as: triethyl citrate, acetyltriethyl citrate, tri-n-butyl citrate, acetyltri-n-butyl citrate, ethyl acetate and the like. For example, the solvent may be used in an amount up to about 50 weight % based on the total weight of solvent and macromer.

The solvent plays several roles in the macromer formulation: (1) viscosity control, (2) control of bubble/foam formation and bubble escape, (3) to enhance tissue penetration, and (4) to provide improved tissue wetting. The viscosity of the formulation ranges from 10 to 100,000 cp, preferably from 500 to 50,000 cp.

Surfactants may also be added to the formulation to control foaming: non-ionic surfactants such as Tween, Brij and siloxanes, as well as ionic surfactants, such as lecithin (phosphatidyl choline), sodium dodecyl sulfate, among others known in the arts.

Catalysts may also be added to the formulation for to increase reaction speed, such as triethylene diamine (DABCO), pyridine, ethyl-2-pyridyl acetate, and stannous octoate.

The color additive that may be utilized in the macromer formulation includes, but is not limited to, methylene blue, FD&C Blue #1 or #2, and conventional color additives that are used in absorbable medical devices such as sutures.

Antioxidants such as butylated hydroxyl toluene (BHT) may be present in the macromer formulation to improve shelf stability of the product.

Adhesive System

One example of an adhesive system includes, but is not limited to, a system where the macromer and a solvent are stored separately until ready for use. For example, the macromer may be stored in one barrel of a double barrel syringe while the solvent is stored in the other barrel. Alternatively, the macromer and the solvent may be mixed by any conventionally means prior to use.

Biocompatible Elastic Gel

The resultant polymer after the in vivo polymerization of the macromer is an elastic gel that is biodegradable, and the degradation products thereof should be both biocompatible and water soluble, so that the degradation products are completely eliminated from the human body as waste products.

Specifically, the macromer or formulation thereof polymerizes to form a biocompatible elastic gel upon contact with water or body fluids, via the following reaction scheme:

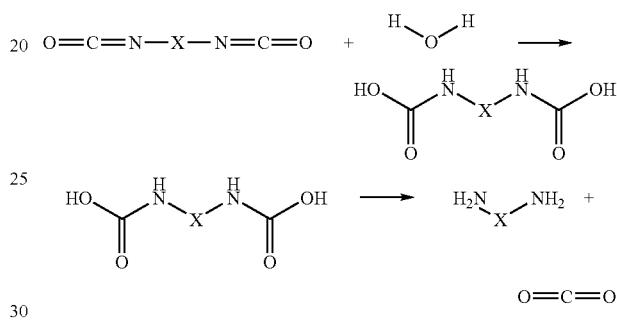

wherein X represent the structural component between the two terminal functional groups and X depends on the type of macromer utilized. The above reaction readily occurs under body conditions resulting in the spontaneuous degradation of the dicarbamate to the diamine and carbon dioxide.

In a subsequent reaction, the newly formed diamine reacts with and isocyanate group to form an elastic gel, via the following reaction scheme:

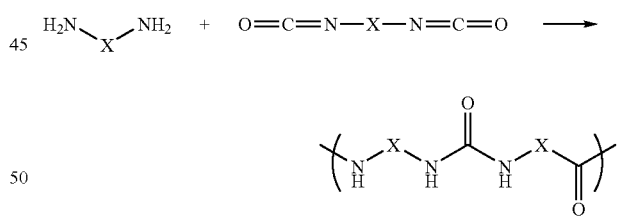

Degradation Products

The elastic gel formed from the macromer described herein is biodegradable and degrades by hydrolysis in vivo to form degradation products, including aromatic degradation products, that are both biocompatible and water soluble. In order to insure water solubility of any aromatic degradation product, the elastic gel is designed to cleave in such a way that the terminal groups on the aromatic degradation product are residues of water-soluble polymers. For example, after the macromer adhesive or sealant formulation polymerizes in the body, the elastic gel that results has the following repeat unit:

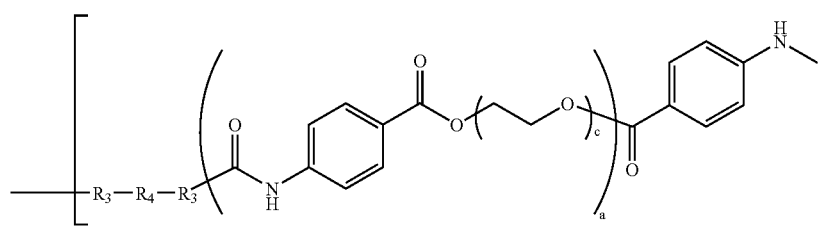

(IV)

where R4, as previously described, is a residue capable of having carboxylate end-groups and the hydrolysable linkages between R3 and R4, are essential to the hydrolytical biodegradability of the elastic gel.

The biocompatible elastic gel (IV) that is formed comprises various hydrolysable linkages, including but not limited to, aliphatic and aromatic ester linkages, urethane linkages and urea linkages. The aliphatic ester linkages in the elastic gel have a higher tendency to degrade in vivo, than the other types of linkages, thereby leaving an initial aromatic degradation product V. While there are other linkages in the aromatic degradation product V fragment that are susceptible to hydrolytic degradation (e.g., urethanes, and aromatic esters), for all practical purposes these do not degrade in vivo to any significant extent before the aromatic degradation product is excreted from the body. For example, the rapidly hydrolysable aliphatic ester linkages between R3 and R4 in the elastic gel degrade within 0-6 months; the more slowly hydrolysable aromatic ester linkages in the aromatic degradation product degrade within 4-24 months; the urethane linkages in the aromatic degradation product degrade within 4 to 24 months; and the very slowly hydrolysable urea linkages in the aromatic degradation product degrade within 24 month to infinity. During the timeframe from implantation of the macromer adhesive or sealant formulation to excretion of the aromatic degradation product V from the body, degradation of the aromatic ester, urethane and urea linkages in the aromatic degradation product V do not occur to any significant extent.

For example let us consider the biodegradation in vivo of a sealant made from PEG400-adipic acid PEG-ester converted into a urethane with PEG4-di benzoyl isocyanate, i.e., structure Ia. After implantation in the body, the elastic gel will initialy degrade hydrolytically into

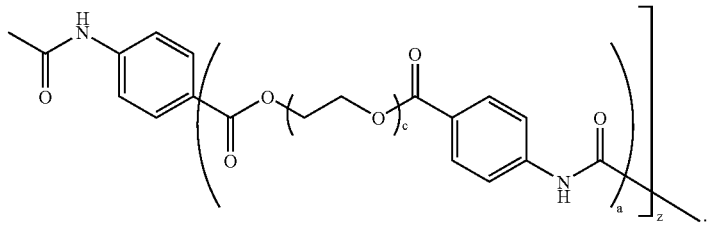

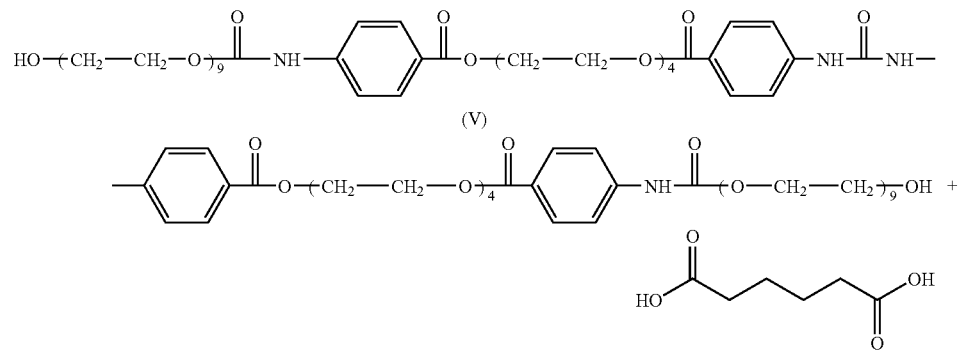

(V)

where all degradation products, including the aromatic degradation product, are essentially water soluble. In particular, the aromatic degradation product is solubilized by the presence of R3, a residue of a water-soluble polymer, as the terminal groups.

This composition has multiple medical applications. For example, as an internal surgical adhesive, the adhesive can bond tissue to tissue, tissue to medical device and medical device to medical device. As a sealant, the composition can be coated on a tissue, or on a medical device, or on the interface of a medical device with tissue to prevent leaks. The composition can be used to form films in situ that may have applications such as for the prevention of surgical adhesions. The composition can be used to form foams in situ that may have applications such as a filler (e.g. dead space removal, reconstructive and cosmetic surgeries), bulking agents, tissue engineering (e.g. scaffolds) materials and others where foams and sponges are useful. The composition can be formulated so that it is injectable and used to form gels in situ that are localized, and adherent to tissue, staying at the site where they are injected. These may have applications such as a delivery matrix for cells and other biologicals, bioactive agents and pharmaceutical or neutraceutical agents, and as embolization agents, and as means to localize contrasting agents. The composition may also be used to attach medical devices (e.g. meshes, clips and films) to tissues. This composition can be used internally in many types of surgery, including, but not limited to, cardiovascular, peripheral-vascular, cardio-thoracic, gynecological, neuro- and general abdominal surgery.

As a surgical sealant/adhesive, it can be used as an adjunct to primary wound closure devices, such as staples, sutures, to seal potential leaks of gasses, liquids, or solids. More specifically, the surgical adhesive/sealant may be applied to a tissue as a part of a surgical procedure, in various forms, for example: liquid, powder, film, sponge or foam, impregnated fabric, impregnated sponge or foam, or spray.

As a filler, the macromer or formulation thereof may be used as a facial, defect or void filler. For example, the formulation may be applied in the interstices of an internal void and allowed to polymerize therein, such that the polymer fills the internal cavities and voids, penetrating and conforming to the interstices and pores of the tissue. The formulation may be used after a broad number of procedures having potential risk of dead space formation, including, but not limited to, radical mastectomy (i.e. breast and regional lymph nodes removal for cancer treatment), breast reconstruction and augmentation procedure, reconstructive or cosmetic abdominoplasty and liposuction, face-lift, cesarean section and hysterectomy in obese patients, orthopedic procedures on thigh region, incisional hernia repair, lipoma excision, and traumatic lesions, i.e. closed trauma.

While the following examples demonstrate certain embodiments of the invention, they are not to be interpreted as limiting the scope of the invention, but rather as contributing to a complete description of the invention.

EXAMPLES

Comparative Prepolymer A1

A polyethylene glycol, Mw 900 g/mol (50 g, 0.056 mol) was dried under vacuum at 120° C. for four hours. Then the polymer was cooled to room temperature under nitrogen and glycolide (12.90 g, 0.11 mol) was added. Stannous octoate was added as a catalyst at 1 mol catalyst: 30,000 mol glycolide. The mixture was continuously stirred under nitrogen and heated to 150° C. for 3 hours. Next the polymer was cooled to 70° C. and paraphenylene diisocyanate (19.57 g, 0.122 mol) was added. This reaction continued under nitrogen with mixing for four hours. The theoretical structure of the resulting prepolymer is:

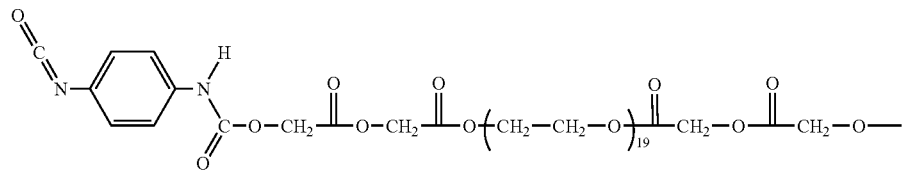
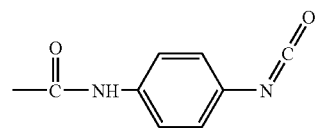

This polymer is a white waxy resin at room temperature.

Example 1

Preparation of Polymers

Prepolymer B1

A 10% solution of ethyl acetate was prepared with 1 mol of tetraethylene glycol, 2.75 mol of 4-nitro benzoyl chloride, and 6 equivalents of sodium carbonate. This reaction was carried out with magnetic stirring under nitrogen at room temperature and atmospheric pressure. The di-nitro intermediate:

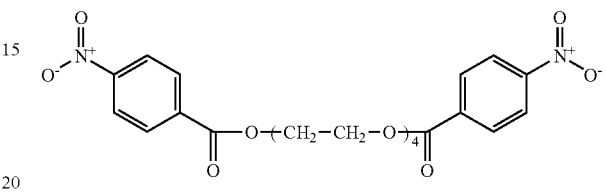

was next hydrogenated. To the ethyl acetate solution containing the dinitro intermediate palladium catalyst (10% Pd on carbon) was added at 5% w/w with vigorous stirring and a hydrogen sparge. This resulted in the di-amine intermediate:

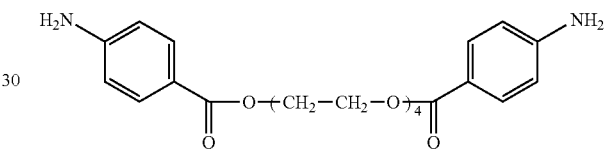

The diamine was purified by washing with aqueous sodium bicarbonate and brine, followed by drying over anhydrous magnesium sulfate. This diamine powder was then dried at 50° C. under vacuum for 12 hours. The purity of the diamine was 99.1% by HPLC.

To prepare the diisocyanate the following procedure was used. In a one liter, three neck flask 68.62 g (0.231 mol) triphosgene and 375 mL of ethyleneglycol diacetate were mixed under nitrogen atmosphere. The resulting suspension was stirred for 20 minutes at ambient temperatures (23° C.). A suspension of 100.0 g (0.231 mol) of PEG-bz-NH₂ (diamine from above) in 333 ml of ethylenglycol diacetate was added within 30 minutes at ambient temperatures (23° C.) to the triphosgene suspension. A thin, slightly yellowish suspension was obtained. The reaction mixture was then heated in the following sequence: to 50° C. (resulting in a pink suspension), then 5 minutes later to 70° C., then 40 minutes later to 90° C. (resulting in a clear solution), then 25 minutes later to 100° C., then 30 minutes later to 115° C., finally, 1 hour later to 130° C. At 130° C. the reaction was stirred for 3 hours and then cooled overnight to ambient temperatures. The following morning the obtained brownish solution was distilled. Distillation started at 94.5° C. (pressure: approximately 1 mbar). After the distillation was finished the temperature of the oil bath was increased to 130° C. to remove residual solvent from the reaction mixture. Yield: 112.5 g, purity 94.7%, 1.1% of residual solvent.

Optionally, as a reaction solvent, instead of ethyeneglycol diacetate, glycerol triacetate (triacetin) was found to yield a product with purity greater than 95%. However, other common solvents, such as toluene, acetone, ethyl acetate, dichloromethane, glyme, 1,4-dioxane, propylene carbonate and acetonitrile, resulted in much lower product purity. Also, conducting the reaction without solvent, results in low product purity.

The resulting product is:

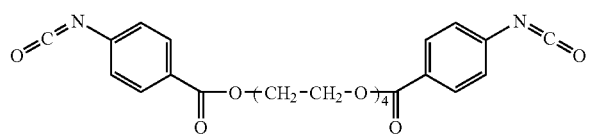

The structure was confirmed by NMR and % NCO titration. The purity was confirmed by performing HPLC on dibutylamine-blocked product. The product is an amber viscous liquid at room temperature.

Prepolymer B2

Polyethyelene glycol, Mw 900 g/mol (0.2 mol) was added to adipic acid (0.1 mol) with polymer bound para-toluene sulfonic acid, at 0.01 mol %. The mixture was heated to 160° C. and water was condensed and distilled with the assistance of a nitrogen purge. Next a vacuum was applied for three hours. The resulting polyol:

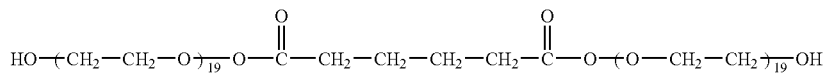

is a clear, colorless low viscosity liquid.

Prepolymer B3

Figure 5:
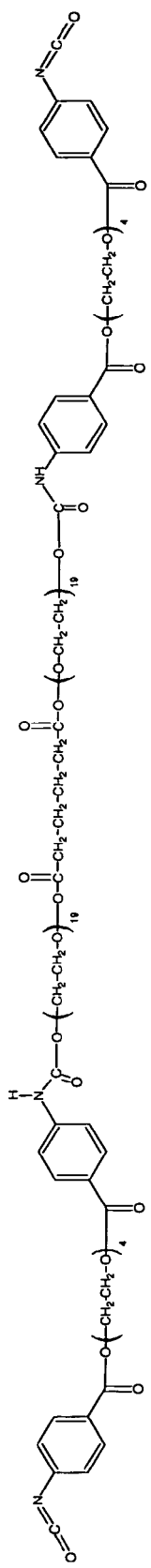
FIG. 5 is a preferred prepolymer B3.

Two mol of prepolymer B1 are added to 1 mol of prepolymer B2 and were mixed and heated to 70° C. for 8 hours under nitrogen. The resulting polymer, a viscous amber liquid at room temperature, is shown in FIG. 5.

Example 2

Preparation of Polymers

Polyester Polyol for Macromer Id

To a clean, dry 250 mL 3 neck flask fitted with nitrogen inlet, temperature probe and dean-stark trap was charged 8.72 g (0.0947 moles) of Glycerin USP. The contents were heated to 120° C. with stirring under nitrogen. Upon reaching temperature, vacuum was applied for 2 hours. Vacuum was released and 32.46 g (0.2845 moles) of Glutaric Anhydride was added. The solution was stirred under nitrogen at 120° C. for 2 hours until IR showed no anhydride present. The solution was cooled and 167.09 g (0.2784 moles) of PEG 600 NF and 0.20 g (0.0009 moles) of Tin (II) Oxalate were added. The flask was heated to 180° C. and held for 2 hours under nitrogen sparge. Vacuum was applied for an additional 17 hours after which the conversion of acid to ester groups was 99.98% based on the acid content. The polyol was cooled to 80° C. and the following were added; 6.13 g of silica-citric acid and 2.38 g of diatomaceous earth. The slurry was stirred at 80° C. under nitrogen blanket for 1 hour. The slurry was diluted to 50% w/v in toluene and stirred for another 15 minutes and filtered through 2-micron cellulose paper. The solvent was evaporated to leave a pale yellow, viscous liquid. Yield=91%, ester conversion=99.73%, Tin content=less than 5 ppm.

Macromer Id

To a clean, oven dried 1 neck 25 mL flask was charged 2.01 g (0.0009 moles) of the Polyester Polyol described in example 2. The polyol was dried under vacuum on a 120° C. oil bath with stirring for 6 hours. The dried polyol was cooled and 2.28 g (0.0047 moles) of Prepolymer B1 from example 1 was added under a nitrogen atmosphere. The mixture was stirred for 20 hours under nitrogen at 70° C. The prepolymer was cooled and diluted to 80% solids in Acetone to yield a viscous amber liquid with a viscosity of ~8,000 cst (25° C.).

Example 3

Preparation of Polymers

Polyester Polyol for Macromer Ic

To a clean, dry 1 L 4-neck flask fitted with mechanical stirrer, nitrogen inlet, temperature probe and dean-stark trap was charged 149.79 g (0.3744 moles) of PEG 400 NF. The contents were heated to 120° C. with stirring under nitrogen. Upon reaching temperature, vacuum was applied for 1.5 hours. Vacuum was released and 85.56 g (0.7499 moles) of Glutaric Anhydride was added. The solution was stirred under nitrogen at 120° C. for 2.5 hours until IR showed no anhydride present. The solution was cooled and 436.06 g (0.7268 moles) of PEG 600 NF and 0.67 g (0.0032 moles) of Tin (II) Oxalate were added. The flask was heated to 180° C. and held for 2 hours under nitrogen sparge. Vacuum was applied for an additional 16 hours after which the conversion of acid to ester groups was 99.96% based on the acid content. The polyol was cooled to 80° C. and the following were added; 6.97 g of silica-citric acid, 7.11 g of diatomaceous earth and 3.39 g of activated carbon. The slurry was stirred at 80° C. under nitrogen blanket for 1 hour. The slurry was diluted to 50% w/v in toluene and stirred for another 15 minutes and filtered through 2-micron cellulose paper. The solvent was evaporated to leave a pale yellow, viscous liquid. Yield=95%, ester conversion =99.88%, Tin content=less than 5 ppm.

Macromer Mixture of Ic:Id in a 1:1 Ratio

To a clean, oven dried 2 neck 250 mL flask fitted with a mechanical stirrer was charged 28.18 g (0.0154 moles) of the Polyester Polyol described in example 3 and 33.90 g (0.0152 moles) of the Polyester Polyol described in example 2. The polyol mix was dried under vacuum on a 120° C. oil bath with stirring for 8 hours. The dried polyol was cooled and 59.38 g (0.0.1224 moles) of Prepolymer B1 from example 1 was added under a nitrogen atmosphere. The mixture was stirred for 20 hours under nitrogen at 70° C. The prepolymer was cooled and diluted to 80% solids in Acetone to yield a viscous amber liquid with a viscosity of ~4,000 cst (25° C.).

Example 4

Preparation of Polymers

Polyester Polyol for Macromer IIb

To a clean, dry 250 mL 3 neck flask fitted with nitrogen inlet, temperature probe and dean-stark trap was charged 53.88 g (0.0842 moles) of Glycerol Ethoxylate $M_n$=1000. The contents were heated to 120° C. with stirring under nitrogen. Upon reaching temperature, vacuum was applied for 2 hours. Vacuum was released and 19.67 g (0.1724 moles) of Glutaric Anhydride was added. The solution was stirred under nitrogen at 120° C. for 3 hours until IR showed no anhydride present. The solution was cooled and 86.99 g (0.0.1449 moles) of PEG 600 NF and 0.20 g (0.0009 moles) of Tin (II) Oxalate were added. The flask was heated to 180° C. and held for 2 hours under nitrogen sparge. Vacuum was applied for an additional 20 hours after which the conversion of acid to ester groups was 99.30% based on the acid content. The polyol was cooled to 80° C. and the following were added; 6.13 g of silica-citric acid and 2.11 g of diatomaceous earth. The slurry was stirred at 80° C. under nitrogen blanket for 1 hour. The slurry was diluted to 50% w/v in toluene and stirred for another 15 minutes and filtered through 2-micron cellulose paper. The solvent was evaporated to leave a pale yellow, viscous liquid. Yield=95%, ester conversion=99.12%, Tin content=less than 5 ppm.

Macromer IIb

To a clean, oven dried 1 neck 50 mL flask was charged 7.03 g (0.0022 moles) of the Polyester Polyol described in example 4. The polyol was dried under vacuum on a 120° C. oil bath with stirring for 6 hours. The dried polyol was cooled and 5.58 g (0.0.0115 moles) of Prepolymer B1 from example 1 was added under a nitrogen atmosphere. The mixture was stirred for 20 hours under nitrogen at 70° C. The prepolymer was cooled and diluted to 80% solids in Acetone to yield a viscous amber liquid with a viscosity of ~15,000 cst (25° C.)

Example 5

Degradation Studies

The test polymer was cast onto glass and allowed to moisture cure under ambient humidity for several hours until a rubbery film was formed. The film was then subjected to the following accelerated hydrolysis conditions. The method consists of hydrolytically degrading a test specimen while maintaining a constant pH by titrating with a standard base and measuring the quantity of base used with time. This measurement and titration is automated by a pH stat instrument (718 STAT Titrator Complete, by MetroOhm, using Software TiNet 2.4). Samples are placed in a 70 mL stirred, sealed, bath of deionized water held at 75° C.+/−0.2° C., and at pH 7.27. Each sample bath is continuously monitored for pH changes (drops in pH) from the set point of 7.27. If any decrease is measured, sodium hydroxide solution is added to return to 7.27 (NaOH 0.05N). The hydrolysis continues until the titrating base is no longer needed to maintain the pH at 7.27. Any undissolved residue is collected, dried and weighed. The mass remaining is reported.

TABLE 2

Degradation Studies of Selected Macromers
(Mass remaining of degraded polymer.
Degraded at 75° C., pH stat 7.27, for 10 days).

| Composition | Wt. % remaining at end |
|---|---|
| Comparative A1 | 30 |
| Inventive B3 | 0.5 |

Table 2 indicates that the water-solubility of the degradation product from the inventive composition B3 is far greater than that of the comparative composition of A1.

Example 6

Burst pressure testing is performed by cutting a linear incision of 0.5 cm in a substrate (pericardium, dura or collagen) and placing the substrate in a test fixture. Sealant is applied to the incision and allowed to cure. Increasing pressure is applied to the transverse side of the substrate using a syringe pump filled with fluid. The maximum pressure is recorded when the sealant ruptures.

TABLE 3

Intestinal Burst Pressure of Selected Macromers

| Macromer | Ic | Ic and Id in a 1:1 ratio | IIb |
|---|---|---|---|
| Burst mm Hg | 28 | 36 | 63 |

What is claimed:

1. A medically acceptable formulation comprising the macromer or mixture thereof of the formula:

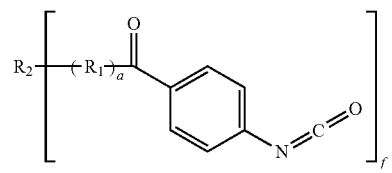

wherein f is two or more; "a" is one to five, $R_1$ is

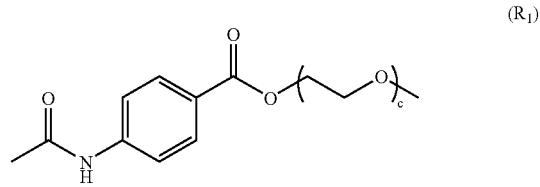

(R₁)

and c is from 1 to 100;

$R_2$ is selected from the group consisting of

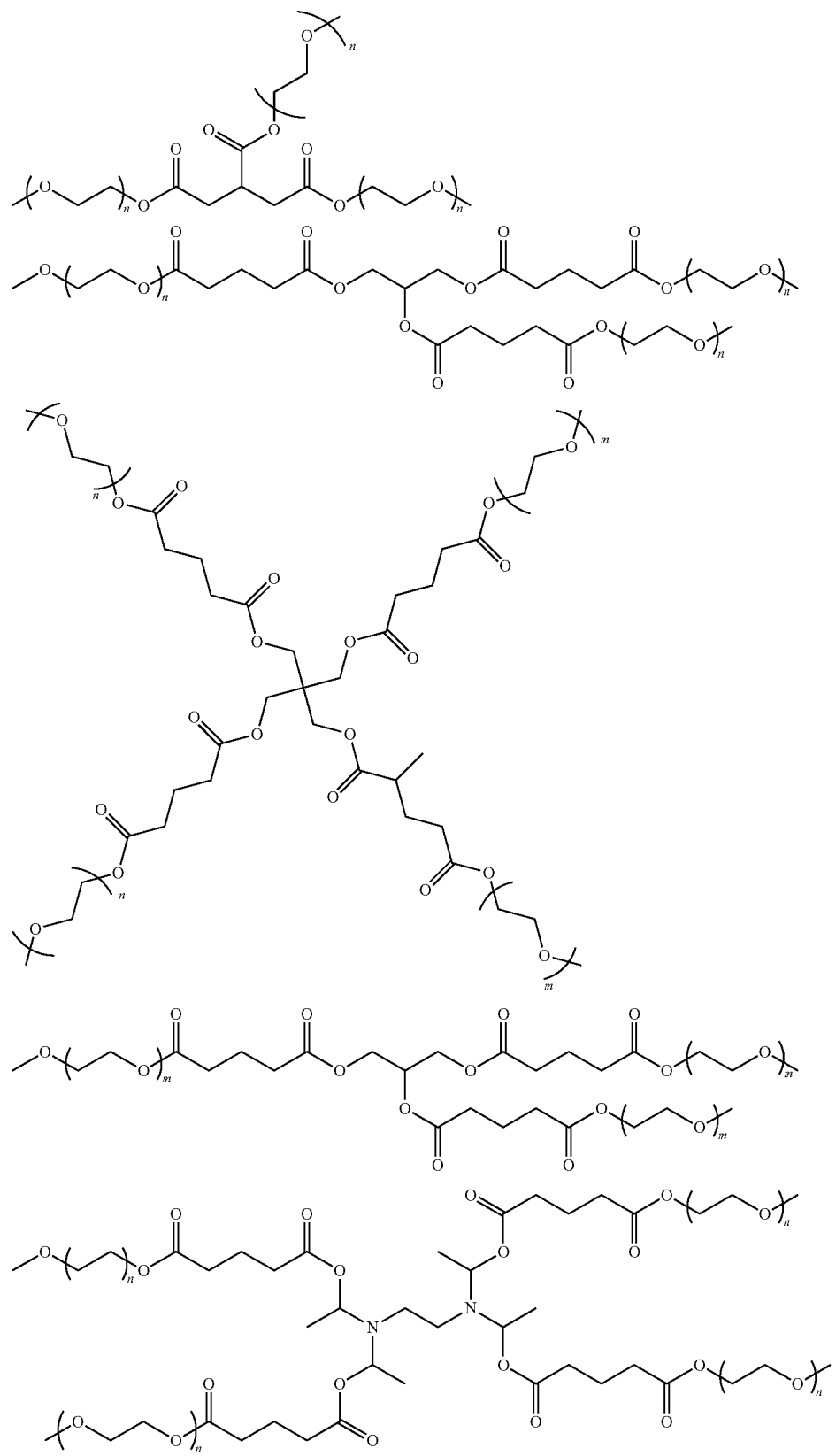

-continued
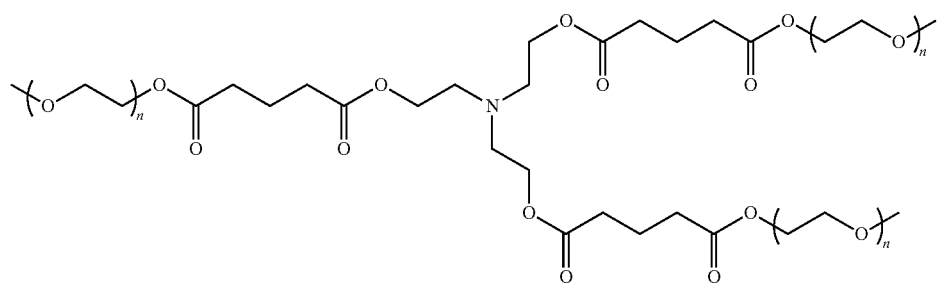
and
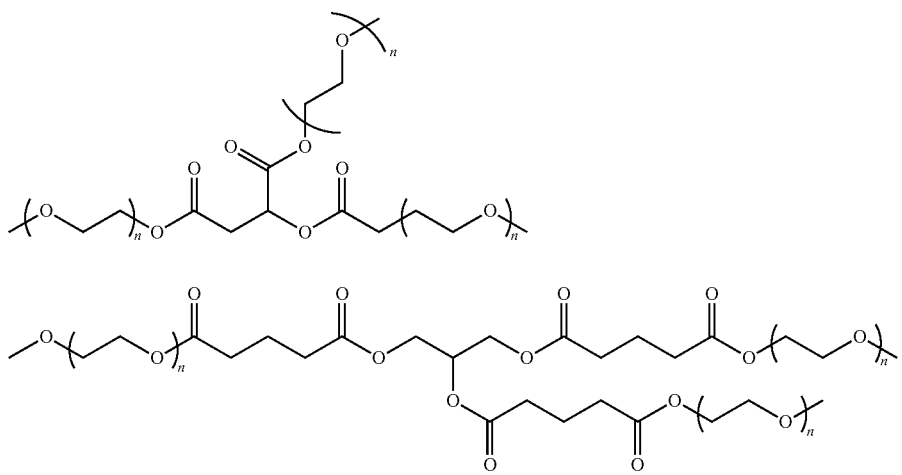
where n is from 2 to 250 and m is from 1 to 10 and at least one solvent.
2. An adhesive system comprising:
 a first housing comprising a solvent; and
 a second housing comprising the macromer or mixture of macromers of the formula:
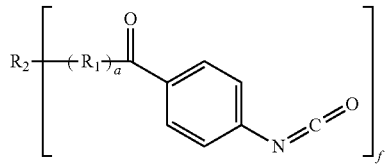
wherein f is two or more; "a" is one to five, $R_1$ is
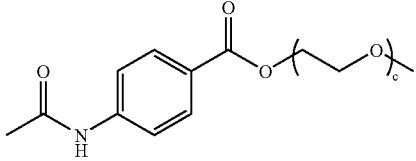 (R$_1$)
and c is from 1 to 100;
$R_2$ is selected from the group consisting of
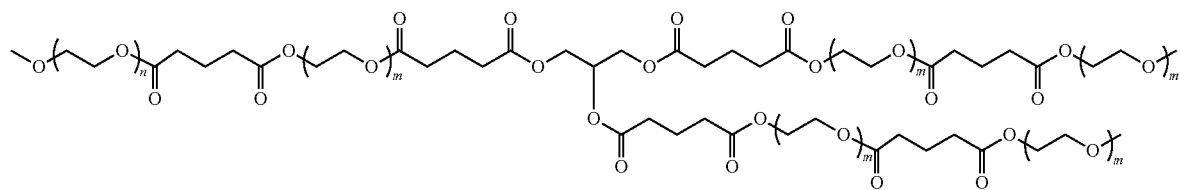

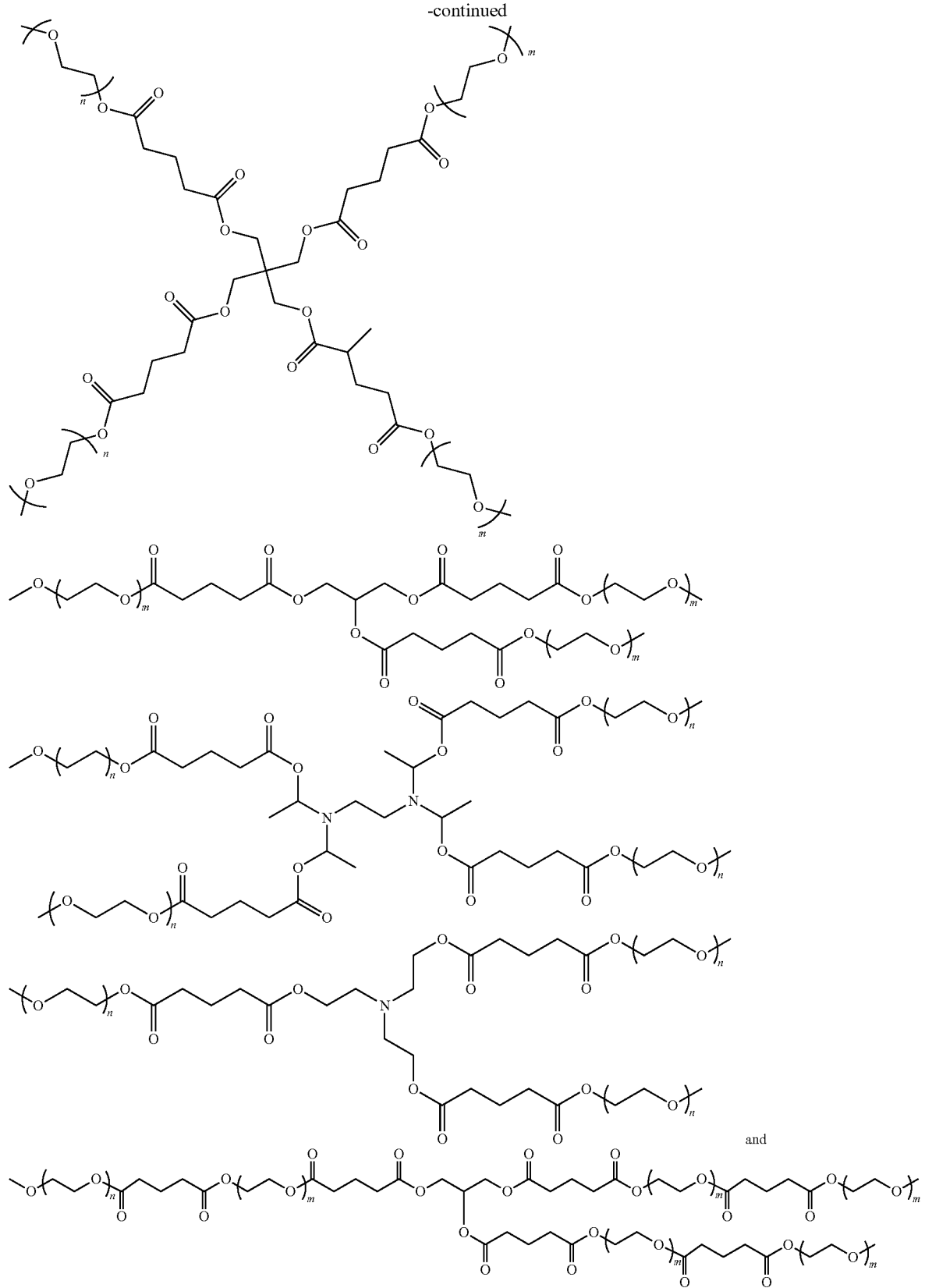
where n is from 2 to 250 and m is from 1 to 10.